(12) United States Patent
Meija et al.

(10) Patent No.: US 7,804,062 B2
(45) Date of Patent: Sep. 28, 2010

(54) BLIND EXTRACTION OF PURE COMPONENT MASS SPECTRA FROM OVERLAPPING MASS SPECTROMETRIC PEAKS

(75) Inventors: Juris Meija, Ottawa (CA); Zoltan Mester, Ottawa (CA)

(73) Assignee: National Research Council of Canada, Ottawa, Ontario (CA)

( * ) Notice: Subject to any disclaimer, the term of this patent is extended or adjusted under 35 U.S.C. 154(b) by 241 days.

(21) Appl. No.: 12/225,861

(22) PCT Filed: Apr. 4, 2007

(86) PCT No.: PCT/CA2007/000615
§ 371 (c)(1),
(2), (4) Date: Oct. 1, 2008

(87) PCT Pub. No.: WO2007/112597
PCT Pub. Date: Oct. 11, 2007

(65) Prior Publication Data
US 2009/0121125 A1 May 14, 2009

Related U.S. Application Data

(60) Provisional application No. 60/789,141, filed on Apr. 5, 2006.

(51) Int. Cl.
*H01J 49/26* (2006.01)
(52) U.S. Cl. ............................ 250/282; 702/22; 702/23; 702/28
(58) Field of Classification Search .................. 702/22, 702/23, 24, 25, 26, 27, 28, 29, 30, 31, 32; 250/281, 282
See application file for complete search history.

(56) References Cited

U.S. PATENT DOCUMENTS

| 4,353,242 | A | 10/1982 | Harris et al. |
| 5,247,175 | A | 9/1993 | Schoen et al. |
| 5,481,476 | A | 1/1996 | Windig |
| 7,105,806 | B2 | 9/2006 | Pappin et al. |

(Continued)

OTHER PUBLICATIONS

Zhang et al., "Weighted Two-Band Target Entropy Minimization for the Reconstruction of Pure Component Mass Spectra: Simulation Studies and the Application to Real Systems", Journal of the American Society for Mass Spectrometer, 2003, 14, pp. 1295-1305.*

(Continued)

*Primary Examiner*—Jack I Berman
*Assistant Examiner*—Nicole Ippolito Rausch
(74) *Attorney, Agent, or Firm*—Hans Koenig

(57) ABSTRACT

A method of obtaining pure component mass spectra or pure peak elution profiles from mass spectra of a mixture of components involves estimating number of components in the mixture, filtering noise, and extracting individual component mass spectra or pure peak elution profiles using blind entropy minimization with direct optimization (e.g. downhill simplex minimization). The method may be applied to deconvolution of pure GC/MS spectra of overlapping or partially overlapping isotopologues or other compounds, separation of overlapping or partially overlapping compounds in proteomics or metabolomics mass spectrometry applications, peptide sequencing using high voltage fragmentation followed by deconvolution of the obtained mixture mass spectra, deconvolution of MALDI mass spectra in the separation of multiple components present in a single solution, and specific compound monitoring in security and/or environmentally sensitive areas.

21 Claims, 7 Drawing Sheets

U.S. PATENT DOCUMENTS

2005/0165560 A1      7/2005  Kushnir et al.
2005/0228591 A1*    10/2005  Hur et al. .................... 702/19
2009/0001262 A1*     1/2009  Visser et al. ............... 250/282

OTHER PUBLICATIONS

Sasaki et al. "Component Analysis of Spatial and Spectral Patterns in Multispectral Images. II. Entropy Minimization", Journal of the Optical Society of America, 1989, 6, pp. 73-79.*
Written Opinion of the ISA on PCT/CA2007/000615, Jul. 30, 2007.
Search Report on PCT/CA2007/000615, Jul. 30, 2007.
Alfassi, Z. B. On the normalization of a mass spectrum for comparison of two spectra. J. Am. Soc. Mass Spectrom. 2004, 15, 385-387.
Brunengraber, H.; Kelleher, J. K.; Des Rosiers, C. Applications of mass isotopomer analysis to nutrition research. Annu. Rev. Nutr. 1997, 17, 559-596.
Chew, W.; Widjaja, E.; Garland, M. Band-Target Entropy Minimization (BTEM): An Advanced Method for Recovering Unknown Pure Component Spectra.Application to theFTIR Spectra of Unstable Organometallics 2002, 21, 1982-1990.
Corana, A., et al., Minimizing Multimodal Functions of Continuous Variables with the Simulated Annealing Algorithm. ACM Trans. Math. Softw. 1987, 13, 262-280.
D'Ulivo, A.; Mester, Z.; Sturgeon, R. E. The mechanism of formation of volatile hydrides by tetrahydroborate(III) derivatization: A mass spectrometric study performed with deuterium labeled reagents. Spectrochim. Acta B. 2005, 60, 423-438.
Duplan, J. C.; Mahi, L.; Brunet, J. L. NMR determination of the equilibrium constant for the liquid H2O—D2O mixture. Chem. Phys. Lett. 2005, 413, 400-403.
Friedman, L.; Shiner, V. J. J. Experimental Determination of the Disproportionation of Hydrogen Isotopes in Water. J. Chem. Phys. 1966, 44, 4639-4640.
Guo, L.; Wiesmath, A.; Sprenger, P.; Garland, M. Development of 2D Band-Target Entropy Minimization and Application to the Deconvolution of Multicomponent 2D Nuclear Magnetic Resonance Spectra. Anal. Chem. 2005, 77, 1655-1662.
Iwata, T.; Koshoubu, J. Minimization of Noise in Spectral Data. Appl. Spectrosc. 1996, 50, 747-752.
Iwata, T.; Koshoubu, J. New Method to Eliminate the Background Noise from a Line Spectrum. Appl. Spectrosc. 1994, 48, 1453-1456.
Kirkpatrick, S.; Gelatt, D. D. J.; Vecchi, M. P. Optimization by simulated annealing. Science 1983, 220, 671-680.
Lee, P. W.-N.; Byerley, L. O.; Bergner, A. E. Mass Isotopomer Analysis: Theoretical and Practical Considerations. Biological Mass Spectrometry 1991, 20, 451-458.
Linbau, F. O.; Christy, A. A.; Kvalheim, O. M. Determination of the Equilibrium Constant and Resolution of the HOD Spectrum by Alternating Least-Squares and Infrared Analysis. Appl. Spectrosc. 1995, 49, 1431-1437.
Meija, J.; Caruso, J. A. Deconvolution of Isobaric Interferences in Mass Spectra. J. Am. Soc. Mass Spectrom. 2004, 15, 654-658.
Meija, J.; Centineo, G.; Garcia Alonso, J. I.; Sanz-Medel, A.; Caruso, J. A. Interpretation of Butyltin Mass Spectra Using Isotope Pattern Reconstruction for The Accurate Measurement of Isotope Ratios From Molecular Clusters. J. Mass Spectrom. 2005, 40, 807-814.
Sturgeon, R.E.; Mester, Z. Analytical Applications of Volatile Metal Derivatives. Appl. Spectrosc. 2002, 56, 202A-213A.
Widjaja, E.; Garland, M. Pure component spectral reconstruction from mixture data using SVD, global entropy minimization, and simulated annealing. Numerical investigations of admissible objective functions using a synthetic 7-species data set. J. Comput. Chem. 2002, 23, 911-919.
Widjaja, E.; Li, C.; Garland, M. Semi-Batch Homogeneous Catalytic In-Situ Spectroscopic Data. FTIR Spectral Reconstructions Using Band-Target Entropy Minimization (BTEM) without Spectral Preconditioning. Organometallics 2002, 21, 1991-1997.
Widjaja, E.; Li, C.; Chew, W.; Garland, M. Band-Target Entropy Minimization. A Robust Algorithm for Pure Component Spectral Recovery. Application to Complex Randomized Mixtures of Six Components. Anal. Chem. 2003, 75, 4499-4507.
Wolfsberg, M.; Massa, A. A.; Pyper, J. W. Effect of Vibrational Anharmonicity on the Isotopic Self-Exchange Equilibria H2X+D2X=2HDX. J. Chem. Phys. 1970, 53, 3138-3146.
Zhang, H.; Garland, M.; Zeng, Y.; Wu, P. Weighted two-band target entropy minimization for the reconstruction of pure component mass spectra: simulation studies and the application to real systems. J. Am. Soc. Mass Spectrom. 2003, 14, 1295-1305.

* cited by examiner

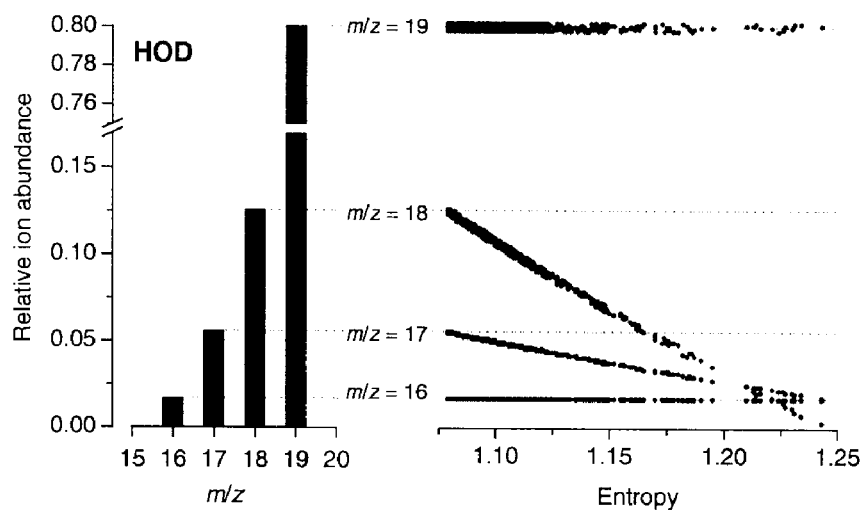
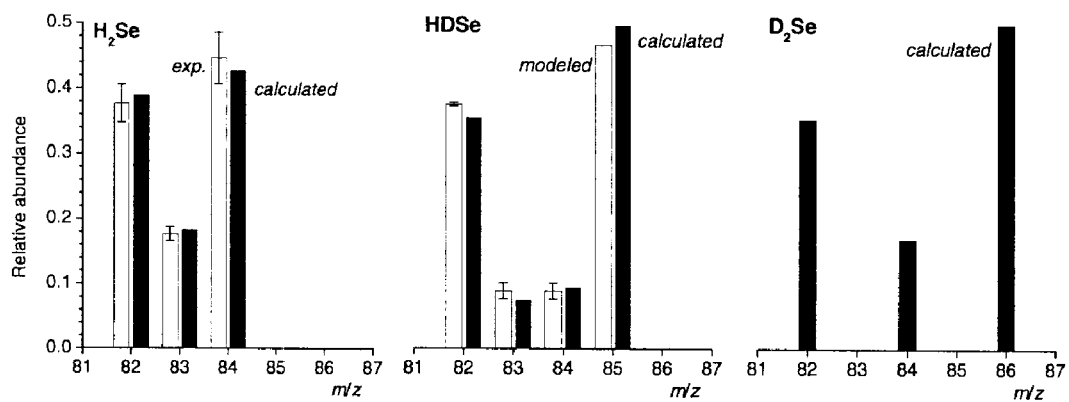
Fig. 1
Fig. 2 time, min

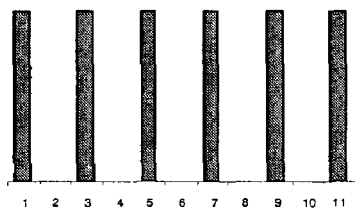
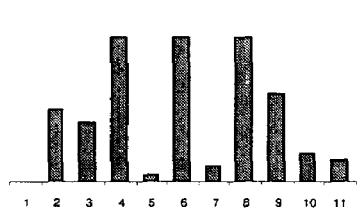
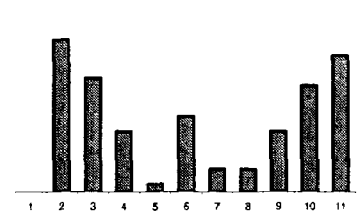
Fig. 10a  Fig. 10b  Fig. 10c
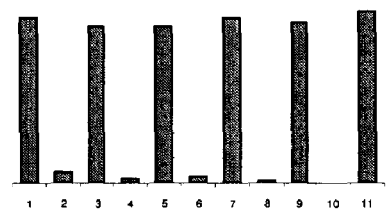
Fig. 11
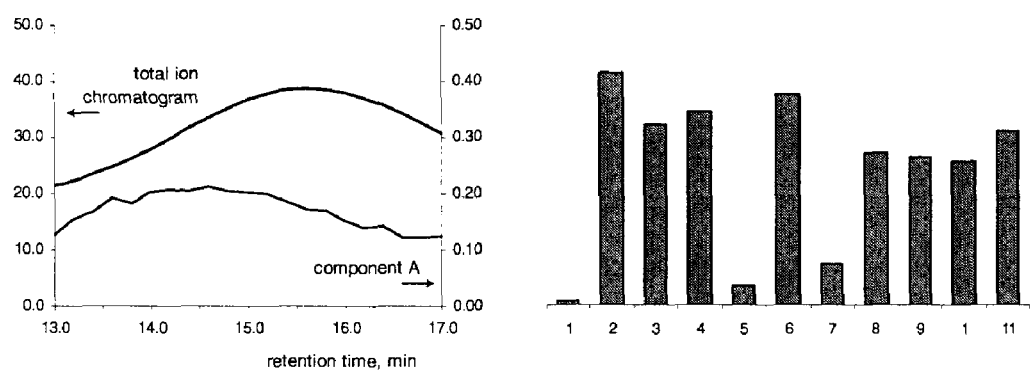
Fig. 12a  Fig. 12b

BLIND EXTRACTION OF PURE COMPONENT MASS SPECTRA FROM OVERLAPPING MASS SPECTROMETRIC PEAKS

CROSS-REFERENCE TO RELATED APPLICATIONS

This application claims the benefit of United States Provisional Patent Application Ser. No. 60/789,141 filed Apr. 5, 2006, the disclosure of which is herein incorporated by reference in its entirety.

FIELD OF THE INVENTION

The present invention relates to extraction of pure component mass spectra from unresolved or partially resolved mixtures. In particular, the present invention relates to methods of identifying compounds in a mixture of compounds and quantification of the compounds in the mixture by mass spectrometric separation and quantification.

BACKGROUND OF THE INVENTION

Majority of overlapping spectra deconvolution approaches operate under the principle that certain prior knowledge about the overlapping component system must be implemented, hence known in advance. There are several existing approaches in achieving this. If the identity of components and hence their pure mass spectra is known in advance, one can use linear algebra protocols, such as those disclosed in U.S. Pat. No. 5,247,175 or U.S. Pat. No. 7,105,806, to find the relative abundances of each component. Similarly, if certain fragment ions are free of interferences (i.e. are not overlapping), the ion chromatograms can be converted into component-chromatograms using the branching ratios obtained from pure standards (US 2005/0165560). Among other approaches, if the peak shapes of the co-eluting components can be modeled or guessed in advance, this information can then be implemented into the deconvolution process (U.S. Pat. No. 4,353,242).

However, there is multitude of situations where none of the above prior information can be known with certainty. Hence, in systems where the actual number of overlapping compounds is unknown and with unknown present components, the above conventional deconvolution algorithms can not be applied. Component identification from such systems in information theory is referred to as the blind deconvolution or blind source separation.

Recently, blind entropy minimization has been used to reconstruct mass spectra of pure components (Zhang, 2003). The method employed by Zhang, 2003 involved the use of a stochastic search algorithm (also known as probabilistic or randomized algorithm), which while effective is too slow to tackle real-life problems.

There remains a need in the art for a deconvolution approach that is both fast and effective for extracting pure component mass spectra from unresolved or partially resolved mixtures of mass spectra.

SUMMARY OF THE INVENTION

It has now been found that multi-variable functions derived from mass spectral data do not have local minima and direct optimization may be used in blind entropy minimization to find the minimum of the function. As a result, minimization is considerably faster than prior art methods.

In an aspect of the invention, there is provided a method of obtaining pure component mass spectra or pure peak elution profiles from mass spectra of a mixture of components comprising: estimating number of components in the mixture; filtering noise; and extracting individual component mass spectra or pure peak elution profiles using blind entropy minimization with direct optimization.

In another aspect of the invention, there is provided a computer readable medium containing instructions for carrying out the method of the present invention. Computer readable media include, for example, magnetic and optical storage media. Some specific examples are hard drives, diskettes, memory sticks, CDs and DVDs.

The present method is generally possible without the use of any prior contextual knowledge about the system and takes advantage of variations of multi-component signal mixtures as they co-elute from a chromatographic column. When each of the components in a multi-component mixture has its own slightly different elution time or response profile (peak shape), it is possible to extract it from the total observed signal using factor analysis-based signal processing. This in turn makes the unwanted analytical variability into a welcome feature in pulling apart the individual components from a heavily overlapping mixture.

After acquiring mass spectral data, analysis of the data (presented, for example, in a data matrix) comprises three main steps: estimation of the number of components present; noise filtering; and, extraction of the individual component spectra.

Estimation of number of components is the first step in most spectral recognition problems. This step also establishes the extent of complexity (number of dimensions). Any suitable algorithm may be used, for example, singular value decomposition or more primitive iterative guessing approaches such as disclosed in U.S. Pat. No. 4,353,242. Singular value decomposition is preferred as it is one of the most rigid algorithms to establish the number of components. In the component mixture context, the singular values are interpreted as the abundance of the chemical components. Hence, small singular values are considered to represent chemical noise whereas large singular values represent detectable chemical components to be identified.

Noise filtering may be accomplished by any suitable method, for example, the classical Savitsky-Golay smoothing. In the context of singular value decomposition, once the number of principal components is identified from the singular value matrix, the noise components may be omitted using a truncated singular value decomposition method of matrix approximation.

The mass spectra of pure components or pure peak elution profiles may be reconstructed using blind entropy minimization as generally outlined by Zhang, 2003, the disclosure of which is herein incorporated by reference. This approach utilizes pattern recognition via entropy minimization. The objective function to be minimized is the entropy of the extracted mass spectrum. In brief, an overall weighted two band-target entropy minimization algorithm can be outlined in the following steps. First, a mass spectral data matrix is compiled where the two dimensions are elution time and m/z scale. Second, singular value decomposition (SVD) of this matrix is performed. This allows identifying components of large (compounds) and low variation (noise) thereby substantially eliminating the components of noise from the main data matrix and establishing the number of components in a single step. Elimination of noise based on this method has been previously utilized in data analysis of mass spectra (Iwata, 1996; Iwata, 1994).

During the SVD decomposition, the noise-filtered data matrix is sub-divided into three smaller matrices:

$$I = U'(\sigma' V^T) \quad (1)$$

With regard to the band-target entropy minimization algorithm there is a connection between two of these matrices and the pure component mass spectra, A, via the (unknown) transformation vector T:

$$A = T(\sigma' V^T) \quad (2)$$

Mass spectral reconstruction of j independent components now becomes a problem of finding the proper T vector for each of the $j^{th}$ component. There are certain restrictions any candidate T vector must comply with. First, pure component spectra have non-negative ion intensities and second, their contribution (concentration) in each of the mixture mass spectra also has to be non-negative. The search for the T vector comprises a calculation of spectrum A from T. Once the A vector is obtained, its entropy with respect to a certain m/z channel (target ion) is calculated as follows: the retrieved component mass spectrum, A, is normalized against the target ion and the entropy of the component spectrum is simply a sum of the individual m/z channel intensities. The search for the proper T vector ends when lowest entropy component mass spectrum is found. Such procedure is repeated for every single monitored m/z channel and the obtained component mass spectra are then inspected for duplicates.

In real-life problems, functions of many variables have a large number of local minima and maxima. Finding the global maximum or minimum of a function can be rather challenging or even impossible. Quite commonly in practice (and as used by Zhang, 2003) multidimensional global optimization problems are solved using stochastic search algorithms (also known as probabilistic or randomized algorithms as these approaches employ a degree of randomness as part of its logic), such as simulated annealing, stochastic tunneling or Monte-Carlo minimization methods. Traditionally, simulated annealing is often used for very hard computational problems where the danger of being trapped in local minima is high (Corana, 1987; Kirkpatrick, 1983). While stochastic approaches are effective, the very slow, limiting their usefulness for commercial application.

Contrary to these approaches, if the multi-variable function to be minimized does not have several local minima, finding the minimum can be achieved considerably faster by using direct optimization methods (steepest descent methods), for example Nelder-Mead downhill simplex minimization method or Levenberg-Marquard minimization. It is a priori impossible to know whether the multi-variable function has several local minima, and the assumption is always made that there are more than one minimum. Unexpectedly, it has now been found that the present multi-variable function derived from mass spectral data do not have local minima and direct optimization may be used to find the minimum of the function. As a result, the method of the present invention is considerably faster (about 100× faster) than previous methods, for example the method of Zhang, 2003.

The method of the present invention can be applied to real-life systems. For example, the method may be applied to deconvolution of GC/MS spectra of overlapping or partially overlapping isotopologues or deconvolution of GC/MS spectra of overlapping or partially overlapping compounds (e.g. pesticides), separation of overlapping or partially overlapping compounds in proteomics or metabolomics mass spectrometry applications, peptide sequencing using high voltage fragmentation followed by deconvolution of the obtained mixture mass spectra, deconvolution of MALDI mass spectra in the separation of multiple components present in a single solution, and specific compound monitoring in security and/or environmentally sensitive areas.

A gas chromatography/mass spectrometry (GC/MS) system involves one or more separation or partial separation systems that creates concentration ratio differences of the components, an ionization source (e.g. electron impact, chemical ionization, etc.), and a mass analyzer (quadrupole mass filter, time-of-flight analyzer, sector field magnetic mass filter, etc.). The concentration gradient is usually achieved using chromatography (gas, liquid, ion, size exclusion, etc.) or any other process that leads to concentration ratio differences (e.g. electrophoresis, ion mobility, distillation, gas effusion, crystallization, manual altering of reaction ingredients). In MALDI mass spectrometry, concentration gradients are produced inherently during sample drying and matrix crystallization process, hence this variable can be successfully utilized for pure component identification in conjunction with band-target entropy minimization deconvolution. Mass spectrometry can be performed using any suitable techniques, for example, atmospheric ionization mass spectrometry (e.g. electrospray ionization, atmospheric pressure chemical ionization) and vacuum ionization mass spectrometry (e.g. MALDI, electron impact ionization, chemical ionization). Electrospray ionization high energy fragmentation mass spectrometry is preferred.

In one particularly advantageous embodiment, using the above deconvolution algorithm, it is also possible to operate an electrospray ionization mass spectrometer constantly in high energy fragmentation mode (often called "front end fragmentation" or "skimmer cone fragmentation", etc) therefore significantly increasing the instrumental duty cycle in comparison to classical peptide sequencing where fragmentation (hence component identification) is performed in a serial scanning fashion with low duty cycle (i.e. MS/MS is performed on pre-selected ions one by one). This way the tandem mass spectra/fragmentation spectra of every eluting peptide can be obtained, thus there is the potential to identify all the co-eluting peptides. However, all fragment mass spectra originating from chromatographically unresolved (overlapping) peptides will be superimposed. Therefore, signal deconvolution is needed to obtain pure peptide tandem mass spectra. The method of the present invention can fulfill this need.

Specific compound monitoring can be achieved by targeting several ions to establish an ion ratio pattern. This can be applied to monitoring of illicit substances, explosives, drugs or environmental pollutants. The above strategy reduces false positives by increasing the detection specificity (since patterns are being detected, and not just the presence of a certain ion).

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which:

FIG. 1 depicts reconstruction of HOD mass spectrum using weighted two band-target entropy minimization.

FIG. 2 depicts reconstructed mass spectra of $H_2{}^{82}Se$, $HD^{82}Se$ and $D_2{}^{82}Se$ using band-target entropy minimization.

FIG. 9b depicts the mass spectrum extracted from the elution profile of FIG. 9a for the 10% component.

FIG. 9c depicts the experimental mass spectrum for the 10% component of the four-component mixture of FIG. 9a.

FIG. 10a depicts individual library mass spectrum component A of a three-component mixture A, B, C.

FIG. 10b depicts individual library mass spectrum component B of the three-component mixture A, B, C.

FIG. 10c depicts individual library mass spectrum component C of the three-component mixture A, B, C.

FIG. 11 depicts a mass spectrum of component A extracted from an elution profile of the three-component mixture A, B, C.

FIG. 12a depicts an elution profile for the three-component mixture A, B, C.

FIG. 12b depicts a mass spectrum of the three-component mixture A, B, C at 14.5 min elution time.

DESCRIPTION OF PREFERRED EMBODIMENTS

Example 1

Extraction of Real-World Unknown Component Spectra

Figure 3:
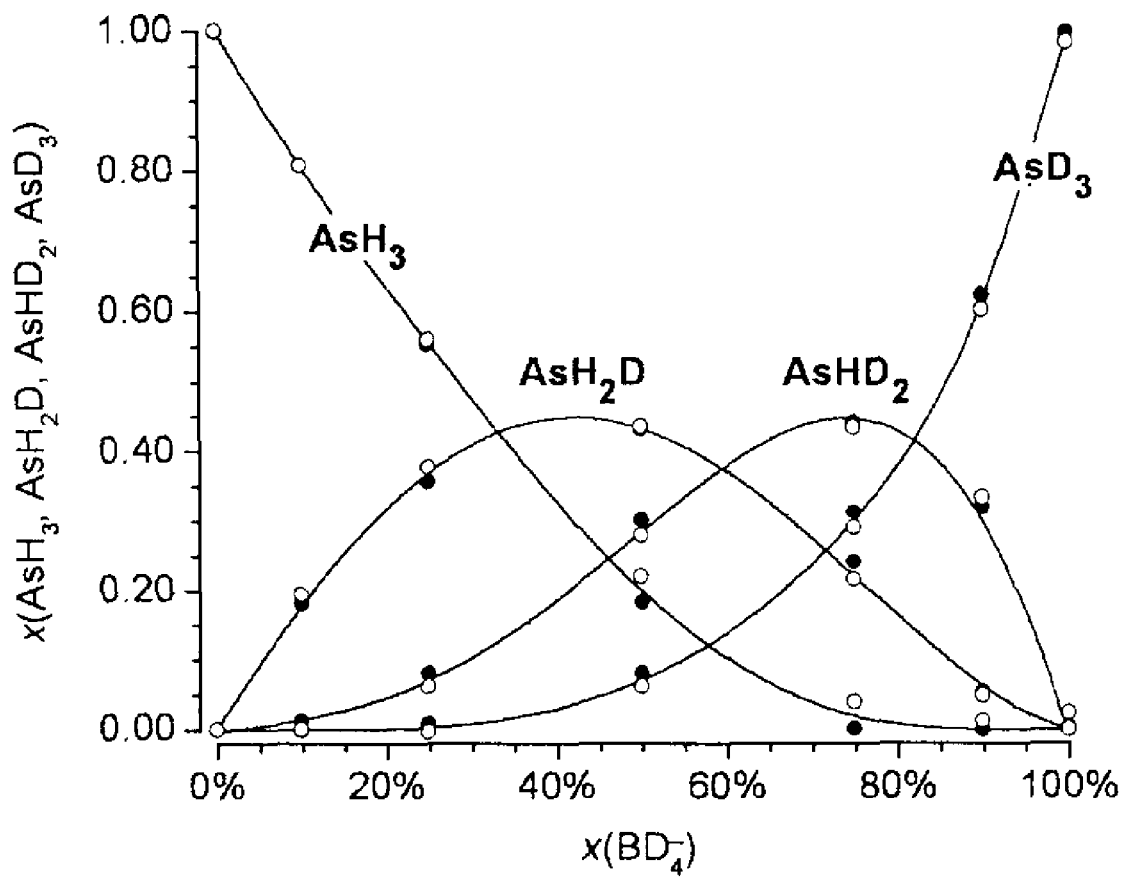
FIG. 3 depicts deconvoluted concentration profiles of arsenic hydride isotopologues generated using various amount fractions of NaBD$_4$ in the mixtures of NaBD$_4$ and NaBH$_4$. Isotopologue mass spectra were obtained from the statistical model (black circles) and the entropy minimization approach (open circles).

This example illustrates the general applicability of blind entropy minimization to the extraction of unknown component mass spectra from the mass spectra of unresolved or partially resolved systems. In this example, blind entropy minimization was conducted in a manner described in Zhang, 2003 using a stochastic optimization technique.

Materials and Methods

Chemicals. The following reagents were used: NaBH$_4$ pellets (Alfa Aesar, Word Hill, Mass.); NaBD$_4$ pellets (99% D, Cambridge Isotope Laboratories, MA); 37%, DCl in D$_2$O (99.5% D, Aldrich); 30% NaOD in D$_2$O (99% D, Aldrich) and D$_2$O (99% D, Aldrich). A solution of NaBH$_4$ prepared in H$_2$O, was stabilized by adding NaOH up to 0.1 M final concentration. A solution of NaBD$_4$ (0.25 M), prepared in D$_2$O was stabilized by adding NaOD up to 0.1 M final concentration.

An enriched isotopic standard solution of 260 μg mL$^{-1}$ $_{82}$Se(IV) in HNO$_3$ aqueous media (Oak Ridge National Laboratory, Oak Ridge, Tenn.) was used to spike the reaction media in septum-sealed vials for cold vapour generation of their corresponding hydrides. All other reagents were of analytical grade.

The following reagents were used: NaBH$_4$ pellets (Alfa Aesar, Word Hill, Mass.); NaBD$_4$ pellets (99% D, Cambridge Isotope Laboratories, MA); 37% DCl in D$_2$O (99.5% D, Aldrich); 30% NaOD in D$_2$O (99% D, Aldrich) and D$_2$O (99% D, Aldrich). A stock solution of NaBH$_4$ (1.0 M) in H$_2$O was stabilized by adding NaOH up to 0.5 M. A stock solution of NaBD$_4$ (1.0 M) in D$_2$O was stabilized by adding NaOD up to 0.5 M. Working solutions of pure 0.2 M NaBH$_4$, 0.2M NaBD$_4$ as well as mixed 0.2 M (NaBH$_4$+NaBD$_4$) were prepared before experiments by adding 4 mL of H$_2$O to x μL of 1.0 M NaBH$_4$+y μL of 1.0 M NaBD$_4$ (x=1000, 900, 750, 500, 250, 100, and 0 μL; x+y=1000 μL). The resulting concentration of NaOH in the final solutions is 0.1 M NaOH. A 0.2 M NaBD$_4$ solution in D$_2$O and 0.1 M NaOD were prepared for hydride generation in fully deuterated reaction medium.

Cold vapor generation of hydrides was performed in septum-sealed vials using solutions of 500 μg mL$^{-1}$ As(III) and Bi(III), and 100-300 μg mL$^{-1}$ (in acidified aqueous media) of $^{123}$Sb(III), $^{73}$Ge(III) and $^{118}$Sn(IV) (Oak Ridge National Laboratory, Oak Ridge, Tenn.). All other reagents were of analytical grade.

Apparatus. A Hewlett-Packard 6890 gas chromatograph operated in the splitless mode and equipped with a Hewlett-Packard 5973 mass selective detector was fitted with a DB-1 capillary column (30 m×0.25 mm i.d.×1 μm; Vallobond VB-1). A gas-tight Hamilton syringe (5 mL) was employed for sampling headspace gases from reaction vials.

Screw cap reaction vials fitted with PTFE/silicone septa (5-10 mL, Pierce Chemical Co.) were used according to experimental requirements. The GC was operated under the following conditions: injector temperature 150° C.; oven temperature 35° C. (isothermal). The carrier gas was He at 1.2 mL min$^{-1}$.

Hydride generation procedure. The 10 mL reaction vial containing 2 mL of acid (1 M HCl or DCl for As, Sb and Bi and 0.01 M HCl or DCl for Ge and Sn), approx. 2-10 μg of the element ions and a Teflon™ coated stir-bar was capped and two stainless steel needles were inserted through the septum. Vigorous stirring of the solution was started and nitrogen was then introduced through one needle in order to purge the atmospheric oxygen from the headspace of the vial. The two needles were then removed and 1 mL of 0.2 M reducing solution (NaBH$_4$, NaBD$_4$ or NaBH$_4$ and NaBD$_4$ mixture) was injected using a plastic syringe fitted with a stainless steel needle. Headspace gases (2-3 mL) were subsequently sampled with a gas tight syringe and injected into the GC/MS.

H₂Se generation procedure. The reaction vial (10 mL) containing 2 mL of 1 M HCl, about 10 μg of $^{82}$Se(IV) and a Teflon™ coated stir-bar was capped and two stainless steel needles were inserted into the septum. Vigorous stirring of the solution was started and nitrogen was then introduced through one needle in order to purge atmospheric oxygen from the headspace of the vial. The two needles were then removed and 1 mL of 0.25 M NaBH₄ solution was injected using a plastic syringe fitted with a stainless steel needle. Headspace gases (2-3 mL) were subsequently sampled with a gas tight syringe and injected into the GC/MS. Mass spectrum of pure H₂Se was obtained.

D₂Se generation procedure. Generation of pure D₂Se was attempted using fully deuterated reaction media. A procedure similar to that described for H₂Se generation was adopted with the following modifications. In a 5 mL vial containing 0.5 mL of 1 M DCl spiked with 0.05 mL of $^{82}$Se(IV) aqueous standard solution, atmospheric oxygen was degassed and 0.5 mL of 0.25 M NaBD₄ solution was injected.

H/D exchange experiments. Pure H₂Se was prepared as described above. Two aliquots of the H₂Se headspace gas (each of 3-5 mL volume) were collected in a rapid sequence. The first aliquot was injected into a 5 mL reaction vial (the exchange vial) containing 1 mL of 0, 3 and 6 M DCl in D₂O and continuously shaken throughout the experiment. The second H₂Se headspace aliquot was injected into the GC/MS to verify the isotopic composition of the synthesized H₂Se. The isotopic composition of the injected hydride in the headspace of the exchange vial was checked at regular intervals by GC/MS. Previous experiments in which H₂Se was injected onto a column pre-treated with DCl vapors have demonstrated that the H/D exchange does not take place in the GC capillary column (D'Ulivo, 2005).

Computations were carried out using the commercially available MathCad v.12.0 package (Mathsoft Engineering & Educ., Inc.). Reconstruction of the mass spectra was done using the statistical mass balance method and the weighted two-band-target entropy minimization algorithm. Concentration profiles of the individual isotopologues were obtained using a least squares isotope pattern reconstruction as described elsewhere. A non-negative least squares minimization routine was used for the reconstruction of more complex Ge and Sn hydride mass spectra to avoid the occurrence of negative contributions (Lawson, 1974). Spectral contrast angle between the two mass spectra was calculated as follows:

$$\cos(a) = \sum_i A_i \times B_i \quad (3)$$

where $A_i$ and $B_i$ are the ion intensities on the $i^{th}$ m/z channel. For spectral comparison purposes, all the mass spectra were normalized with respect to their $L^2$-norm, i.e. $\Sigma A_i^2 = \Sigma B_i^2 = 1$, unlike the conventional $L^1$-norm ($\Sigma A_i = \Sigma B_i = 1$) for the reasons discussed elsewhere (Alfassi, 2004).

Reconstruction of HOD Mass Spectrum

Mass spectra of pure components can be reconstructed using entropy minimization as recently outlined by Zhang, 2003. In essence this approach is a pattern discovery (recognition) via entropy minimization. The objective function to be minimized thus is the entropy of the extracted mass spectrum. In information theory entropy is a measure of the average amount of information required to describe the distribution of some variable of interest. The most commonly used measure of entropy was introduced by Shannon (S=p·lnp) (Shannon, 1949). This classical entropy definition was previously used in reconstruction of continuous NMR, Raman and IR spectra where p has been quantitatively linked with the first or higher order derivatives (Guo, 2005; Chew, 2002; Widjaja, 2002; Widjaja, 2003). However, such an entropy definition (smoothness of the spectra) cannot be transferred in the context of mass spectrometry where the individual masses are discrete by their nature, thus a modified non-logarithmic entropy definition is used in this model recently developed by the Garland group.

An overall weighted two band-target entropy minimization algorithm can be outlined in the following steps. First, a mass spectral data matrix $I_{k \times n}$ is compiled from k mass spectra each having n mass-to-charge channels (k≥number of possible isotopologues). Each mass spectrum is normalized to unity total ion intensity. Second, a singular value decomposition of $I_{k \times n}$ matrix is performed. This procedure represents any k×n matrix as a product of three matrices ($U_{k \times n}$ and $V_{n \times n}$ are orthonormal, e.g. $U^T U = V^T V = 1$):

$$I_{k'n} = U_{k'k'} \sigma_{n'n'} V_{n'n}^T \quad (4)$$

This leads to the diagonal singular value matrix Σ and the right singular value matrix $V^T$. The obtained singular value decomposition is used further for noise reduction. The main idea is that the experimental $I_{k \times n}$ matrix contains components of large and low variation. It can be shown that the small singular values in Σ mainly represent the noise. This noise is eliminated by keeping only the first j non-zero singular values (j≤k). It is worth mentioning that the Σ matrix rang (which equals j) represents the number of individual compounds whose spectra are to be deconvoluted. The filtered (truncated) representation of spectral matrix $I_{j \times n}$ now becomes $$I_{j'n} = U_{jj'} \dot{\sigma}_{jj'} V_{j'n}^T \quad (5)$$

The pure component mass spectra can be obtained using the transformation matrix T:

$$A_{1'n} = T_{1j'} (\dot{\sigma}_{jj'} V_{j'n}^T) \quad (6)$$

The presence of matrix Σ in this equation serves as a weighting procedure making the model more robust. Mass spectral reconstruction of j independent components now becomes a problem of finding all T vectors. There are certain restrictions any candidate T vector must comply with. First, it has to produce a non-negative pure component spectrum estimate $A_{1 \times n}$. Choosing the two target bands (m/z channels) $A_x$ and $A_y$ is the crucial step of the method. During this step $A_{1 \times n}$ matrix is normalized with respect to the total intensity of the target bands:

$$A^*_{1'n} = \frac{A_{1'n}}{A_x + A_y} \quad (7)$$

Depending on the targeted m/z channels, mass spectra of different isotopologues are extracted. For example, targeting the m/z=18 and 20 yields a mass spectrum of D₂O, targeting m/z=17 and 18 yields a H₂O mass spectrum and targeting m/z=17 and 19 or 18 and 19 results in retrieval of the HOD spectrum. Second, component contribution (concentration) in each of the k mass spectra also has to be non-negative:

$$c_{k'1} = I_{k'n}' A^*_{n'1}{}^T (A^*_{1'n}' A^*_{n'1}{}^T)^{-1} \quad (8)$$

The objective function (entropy) to be minimized is simply the sum of the channel intensities in the reconstructed mass spectrum:

$$\min(G) = \mathring{a}_n A_{1'n}^* \quad (9)$$

Minimization of the objective function (in terms of T vector) is usually optimized using the simulated annealing algorithm which is a good choice for a global minimum search in many dimensions. In this situation the number of dimensions is small (three for the $H_2O/HOD/D_2O$ system) therefore an exhaustive random search was used.

As mentioned above, the model seeks the lowest entropy (most simple) mass spectra within the non-negativity constraints. In a particular $H_2O/HOD/D_2O$ example, the three component concentration and mass spectral information is condensed into five spectral channels therefore the system is undetermined and an infinite number of HOD mass spectra can be obtained. Since one of such possible solutions is a HOD spectrum with no fragment ions, this is the obvious minimum entropy result (the simplest mass spectrum). In other words, additional contextual information is needed to separate the mathematical solution from the chemically meaningful solution of the HOD mass spectrum. The same applies to the reconstruction of the HDSe mass spectrum. The blind deconvolution lowest entropy result for the HOD mass spectrum is (0.000; 0.000; 0.000; 1.000; 0.000). This result clearly has no chemical meaning, especially considering the experimentally measured mass spectra of $H_2O$ and $D_2O$. When the abundance of the HOD molecular ion is set within the range of $H_2O$ and $D_2O$ molecular ions, the reconstructed mass spectrum of HOD using the weighted two-band target entropy minimization algorithm (targeting m/z=18 and 19) with the above mentioned restriction of molecular ion intensity is (0.017; 0.056; 0.126; 0.801; 0.000) as shown in FIG. 1. Although these two results are quantitatively different, nevertheless, they are nearly identical when compared using the spectral contrast angle (99% similarity). It is clear that the spectral contrast angle is not a good choice for comparing the experimental and the reconstructed spectra due to its insensitivity to low intensity ions. This was also recently pointed out by Zhang et al. (2003) who proposed using the ratio of the geometric and the arithmetic means as a similarity measure between the mass spectra. Using this criterion, the similarity between constrained and unconstrained HOD spectra becomes 89%. In the first unconstrained band-target entropy minimization reconstruction of mass spectra, the Garland group achieves 76-92% similarity (calculated using the ratio of geometric and arithmetic means) between the reference and measured spectra in a four component mixture (ethanol, acetone, hexane and toluene in the m/z=10-100 range).

It is evident that when dealing with underdetermined overlapping isotopologue systems, ion intensities in the extracted pure component mass spectra can be biased if no contextual feedback is provided. As has been seen, although such bias might be of little importance for spectral recognition, it is, nevertheless, significant for quantitative purposes.

Reconstruction of HDSe Mass Spectrum

Reconstruction of selenium hydride mass spectra is a problem similar to that of the water example above. The difficulty of pure component spectra reconstruction, however, is increased due to the fact that the $D_2Se$ mass spectrum is difficult to obtain even by reaction of trace amounts of Se(IV) with $NaBD_4$ in deuterium-only medium ($DCl+NaBD_4$, x(D) >97% at.) as discussed previously in the materials and methods section.

Accordingly, alternating least squares cannot be used to reconstruct the mass spectrum of HDSe since no experimental estimate of $D_2Se$ is available. In spite of this, FIG. 2 shows the entropy minimization estimates of $H_2Se$, HDSe and $D_2Se$ mass spectra (containing only $^{82}Se$ isotope). The $H_2Se$ mass spectrum was recovered by targeting the m/z=82 and 84, HDSe by targeting m/z=82 and 85 and the $D_2Se$ mass spectrum was recovered by targeting the m/z=82 and 86. To reduce the bias in recovered ion intensities, the molecular ion in the HDSe mass spectrum was forced to be in the range of $H_2Se$ and $D_2Se$ molecular ion intensities. One can see that the reconstructed $H_2Se$ mass spectrum agrees well with the experimental measurements (FIG. 2).

Quantification of Isotopologues Using Reconstructed Mass Spectra $H_2O/HOD/D_2O$. Mixtures of $H_2O$ and $D_2O$ are characterized by the equilibrium $H_2O+D_2O=2HOD$ and isotopic self-exchange reaction of water in gaseous or liquid phases has been the subject of numerous investigations and debates over the past decades. Although seemingly simple system, estimates of the $H_2O/D_2O$ isotope exchange equilibrium constant (in both gaseous and liquid phases) are range between 3.41 and the geometric mean of 4.0. This value has been recently (re)estimated using IR and NMR techniques.

Using the above described HOD reconstruction/deconvolution algorithm, the equilibrium constant can be calculated from the amount fractions of $H_2O$, HOD and $D_2O$. Replicate measurements in the range of x(D)≈50-70% lead to the average value of K=3.85±0.03 (±2s) using the entropy minimization model. This is in good agreement with the "best" theoretical value of 3.85. The two most recent liquid phase equilibrium constant measurements (at 298 K) are 3.86±0.07 and 3.86±0.01 (Libnau, 1995; Duplan, 2005). Previous direct mass spectrometric measurements (carried out in the 1960's) have led to similar the values; however, these measurements have been performed at electron accelerating voltages of 3 eV to eliminate any fragment formation (Friedman, 1966). Although this classical approach avoids the need for deconvolution, it is clearly not of practical use for a variety of analytical purposes due to the deterioration of method sensitivity and robustness.

$H_2Se/HDSe/D_2Se$. Various gaseous mixtures of $H_2Se/HDSe/D_2Se$ were obtained when $H_2^{82}Se$ (generated from $^{82}SeO_3^{2-}$ and 2 M $HCl/NaBH_4$) was introduced in the headspace of $D_2O/DCl$ environment. In such conditions rapid H/D exchange takes place resulting in a rise of $HD^{82}Se$ and $D_2^{82}Se$ concentrations in the headspace. The resulting mixtures were then analyzed using GC/MS and their composite mass spectra were decomposed using the weighted two band-target entropy minimization algorithm. The relative amount fractions of isotopologues as obtained from both models are in good agreement and are not biased.

Based on reaction purities of reagents, the estimated H atom fraction in the reaction solution was <7%. The obtained mixture contained 43% $H_2Se$ and 44% HDSe and only 13% $D_2Se$ (63% atom fraction of H). Decreasing the volume of the spike of $^{82}Se(IV)$ aqueous standard solution to 0.01 mL (H atom fraction in reaction solution <3%) improved the purity of the $D_2^{82}Se$, but it was unsuccessful in the production of pure $D_2Se$: the composition of the resulting mixture was 10% $H_2Se$, 26% HDSe and 64% $D_2Se$. Total hydrogen incorporation in this mixture is 23% which is far from the isotopic distribution of the solvent (3% H and 97% D). The present findings contradict the previous hypothesis which assumed that the isotopic composition of hydrogen selenide is similar to that of the solvent due to the rapid H/D exchange (as a consequence of the strongly acid nature of $H_2Se$ and $D_2Se$).

Deuterium Containing Hydrides of As, Sb, Bi, Sn And Ge

Deconvolution of $EH_3/EH_2D/EHD_2/ED_3$ mass spectra. One of the most prominent features of band target entropy minimization is the selection of the target m/z channels. Given a mass spectra with n channels there are $\frac{1}{2} \cdot n(n+1)$ combinations of two-band targets (including situations where both bands represent the same m/z channel). In the case of arsenic hydride mixtures, 28 different targets over a seven channel mass spectra (m/z=75-81) leads to four distinct mass spectra. An important aspect for retrieving a component mass spectrum using this technique is the existence of a unique m/z channel that bears the highest intensity ion among all the other component spectra. $AsH_3$ has such an ion at m/z 78, $AsH_2D$ at m/z 79, $AsHD_2$ at m/z 80 and $AsD_3$ at m/z 81.

Two of the four mass spectra are in agreement with the experimental spectra of $AsH_3$ and $AsD_3$; however, closer inspection of the remaining two spectra showed abnormally large molecular ions. This is not consistent with the observed ion intensity relationships in isotopologue mass spectra since it is reasonable to assume that the molecular and elemental ion intensities of isotopologues have to range between the intensities of fully hydrogenated and deuterated compounds. When such contextual knowledge was included in the entropy minimization algorithm the obtained $AsH_2D$ and $AsHD_3$ mass spectra were in good agreement with a standard statistical model.

Deconvolution of $EH_4/EH_3D/EH_2D_2EHD_3/ED_4$ mass spectra. Aqueous phase reaction of borohydride, $BH_4^-$, with Ge(IV) and Sn(IV) species forms $GeH_4$ and $SnH_4$ respectively. However, in the presence of deuterated borohydride, $BD_4^-$, four more hydrides can form: $EH_3D$, $EH_2D_2$, $EHD_3$, and $ED_4$ (E=$^{73}$Ge, $^{118}$Sb) depending on the $BH_4^-/BD_4^-$ ratio. Also, various partially deuterated hydrides can be obtained when $GeH_4/GeD_4$ and $SnH_4/SnD_4$ are subjected to H/D exchange reactions at different pH.

Germanium and tin hydride mass spectra are different from the As, Sb and Bi hydride in a sense that the molecular ion is practically absent. Also, the number of isotopologues is larger by one than in the case of group V element hydrides. For these reasons the Ge and Sn hydride isotopologue mass spectra substantially overlap and the retrieval of all five isotopologue mass spectra using the entropy minimization model is impossible. $GeH_4$, $GeD_4$ and $SnH_4$, $SnD_4$ mass spectra can be easily recovered using the restrictions analogous to As, Sb and Bi spectra. Alternating the band-targets for germanium hydride mixtures, for example, leads to the retrieval of only $GeH_4$, $GeD_4$ and $GeHD_3$ spectra. Accurate ion intensities, however, cannot be ensured for $GeH_3D$, $GeH_2D_2$, $GeHD_3$ and their Sn analogues for two reasons. First, no feasible verification of the ion intensities can be done (due to the absence of the molecular ions) and, secondly, there is no safe way to ensure that pure spectra (and not linear combinations of several spectra) are retrieved from the entropy minimization. From this it is clear that entropy minimization cannot be used to extract the reference spectra of $GeH_3D/GeH_2D_2$ and $SnH_3D/SnH_2D_2$. Despite the difficulties of implementing the entropy minimization model, it has an important advantage in retrieval of fully deuterated hydride reference spectra. Due to the high reactivity of $GeD_4$ and $SnD_4$, the H/D exchange process makes it extremely hard to obtain mass spectra with no impurities from the first exchange products $GeHD_3$ and $SnHD_3$.

Validation of the reconstructed mass spectra. Although it is practically impossible to obtain pure mass spectra of the partially deuterated species (unless scrupulous separation is performed), nevertheless, it is possible to obtain experimental evidence of certain ion ratios for the $AsHD_2$, $SbHD_2$ and $BiHD_2$ mass spectra from rather simple experiments. When $^{75}$As, $^{123}$Sb and $^{209}$Bi hydrides are generated in an environment that contains >90% deuterium (as $BD_4^-$), it is reasonable to assume that the generated hydride mixtures will contain mostly $^{75}AsD_3$, $^{123}SbD_3$, $^{209}BiD_3$, some amounts $^{75}AsHD_2$, $^{123}SbHD_2$, $^{209}BiHD_2$, and virtually no other species such as $AsH_3$ or $AsH_2D$. The same principle is also observed, for example, in a $H_2O/HOD/D_2O$ system. In such mixtures ions with even m/z ratios originate from the $^{75}AsHD_2$, $^{123}SbHD_2$, and $^{209}BiHD_2$ and have no contributions from the fully deuterated compounds. Thus, the even m/z ion ratios can be compared to the theoretical estimates from entropy minimization models as shown in Table 1. Hydrides for this experiment were generated using a 90:10 mixture of equimolar $NaBD_4$ and $NaBH_4$ solutions.

TABLE 1

Validation of the reconstructed mass spectra

| Ions | m/z | Experimental[a] | Entropy model[b] |
|---|---|---|---|
| $^{75}AsHD_2 \cdot ^+/^{75}AsHD^+$ | 80/78 | 5.26 ± 0.55 | 8 ± 5 (38 ± 10) |
| $^{75}AsHD_2 \cdot ^+/^{75}AsH \cdot ^+$ | 80/76 | 2.04 ± 0.15 | 3.1 ± 0.5 (7.8 ± 1.0) |
| $^{123}SbHD_2 \cdot ^+/^{123}SbHD^+$ | 128/126 | 3.85 ± 0.14 | 4.0 ± 1.4 (n/a)[c] |
| $^{123}SbHD_2 \cdot ^+/^{123}SbH \cdot ^+$ | 128/124 | 2.33 ± 0.03 | 2.5 ± 0.6 (19 ± 8) |
| $^{73}GeHD_3 \cdot ^+/^{73}GeHD_2^+$ | 78/76 | 1.5 ± 0.4 | n/a (2.0 ± 0.5) |
| $^{118}SnHD_3 \cdot ^+/^{118}SnHD_2^+$ | 123/121 | 3.1 ± 0.3 | n/a (n/a)[d] |

[a]Obtained from the $AsD_3/AsHD_2$ and $SbD_3/SbHD_2$ mixtures generated with $NaBD_4$ + $NaBH_4$ (90:10) (±2 s are reported). $SnHD_3/SnD_4$ and $GeHD_3/GeD_4^\bullet$ mixtures were obtained from $NaBD_4$ in $H_2O$.

[b]Constrained entropy minimization (restrictions in the molecular ion intensity were applied). Values obtained from blind deconvolution are given in the parenthesis.

[c]m/z = 126 intensity is very small (~0.004) in blind deconvolution.

[d]m/z = 121 intensity is very small (~0.01) in blind deconvolution.

It is evident from these data that unconstrained (blind) entropy minimization may lead to biased ion ratios. Nevertheless, the blind entropy minimization leads to mass spectra that are in agreement with experimental evidence. Applying restrictions on particular ion intensities is, perhaps, feasible, only in isotopologue systems where partial knowledge is always present (since the molecular formulas are known). Similarly, it is possible to obtain accurate spectral intensities from the band-target entropy minimization algorithm when certain m/z channels are forced to zero (as in the case of the $GeD_4$ mass spectra). In practice, such restriction can be useful when the task is to extract the mass spectrum of a particular component. For example, when a mass spectrum of $AsH_3$ is required, the intensities of the channels 75>m/z>78 can be set to zero.

Concentration profiles of isotopologues. The ultimate aim of this study was to be able to obtain accurate concentration profiles for the deuterated element hydrides. To achieve this, various ratios of $BH_4^-/BD_4^-$ were used to generate the arsenic hydrides and the collected normalized mass spectra (m/z=75-81) of the hydride mixtures were then inspected. Amount fraction of each compound in the analyzed gas mixtures was calculated from the observed composite mass spectra using the isotope pattern reconstruction. In this procedure, the amount fractions of all four arsenic hydride isotopologues are obtained from the least squares fit of the following equation:

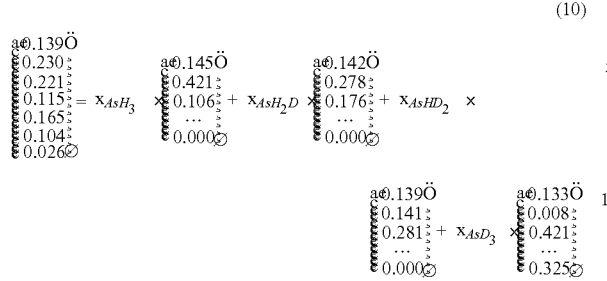
(10)

The left side of the equation is the average mixture mass spectrum (from n=4 experiments) and right side contains the four mass spectra of the individual isotopologues. Least squares fitting of this mass spectrum leads to the relative isotopologue abundances 0.18, 0.43, 0.31 and 0.09 for $AsH_3$, $AsH_2D$, $AsHD_2$ and $AsD_3$ respectively. FIG. 3 shows the deconvoluted concentration profiles of the arsenic hydride isotopologues generated using various amounts of $NaBD_4$ in the mixture of $NaBD_4$ and $NaBH_4$ (from pure $NaBH_4$ to pure $NaBD_4$). From these profiles one can see that the sequential hydrogen and deuterium incorporation into the metal hydrides approximately follows the binomial probability distribution:

$$x_{AshH_{3-i}D_i} = \frac{3!}{i! \times (3-i)!} \times x_D^i \times x_H^{3-i} \quad (11)$$

where $x_D$ and $x_H$ are the deuterium and hydrogen amount fractions in the borohydride mixtures ($BD_4^-/BH_4^-$). Any deviations from this equation are the result of kinetic effects of H and D transfer. Increasing the amount of deuterium in the borohydride results in the systematic increase of deuterated arsenic hydrides: starting from the $AsH_2D$, then followed by $AsHD_2$ and ultimately, $NaBD_4$ produces almost pure $AsD_3$.

Thus, band-target entropy minimization can extract $EH_2D$ and $EHD_2$ mass spectra from a mixture of isotopologues with unknown concentration. Accurate ion intensities can be predicted for these compounds. Using the predicted mass spectra it is possible to estimate individual isotopologue concentration in unknown mixtures.

Example 2

Entropy Landscape Surface Properties for a Simulated Two-Component Pesticide System Example 1 demonstrates the utility of blind entropy minimization for the extraction of unknown component mass spectra from the mass spectra of unresolved or partially resolved real-world systems. Example 2 describes the use of blind entropy minimization in the context of extracting individual mass spectra of a simulated two-component pesticide mixture. Specifically, Example 2 demonstrates the properties of entropy surface landscape and its advantages in mass spectral deconvolution.

In an arbitrary chosen system of two components, the extracted mass spectra (not necessarily pure) is a function of the T vector (containing two variables a and b):

$$A = (a\,b) \cdot \sum_{const} \cdot V^T \quad (12)$$

Hence, the entropy landscape of the extracted mass spectra, A, can be explored as a two-variable function:

$$S = f(a,b) \quad (13)$$

Figure 4:
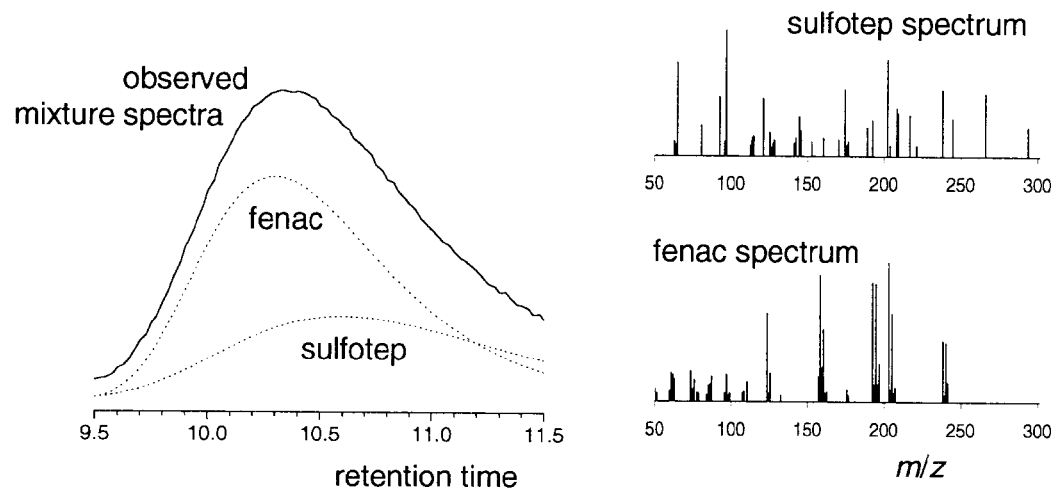
FIG. 4 depicts reference mass spectra for the pesticides sulfotep and fenac and a simulated overlapping chromatographic elution profile for a mixture of sulfotep and fenac.

This two component system entropy surface landscape can be visualized as a 3D scatter plot. For this purpose, an overlapping chromatogram of two-component mixture of two pesticides (fenac and sulfotep, using ions from m/z=50 to 300) was simulated with added proportional white noise. For this purpose, reference spectra of the pure compounds were obtained from the NIST mass spectral library, and an overlapping chromatographic elution profile was then established using exponentially modified Gaussian peak profiles (tailing peaks) with added noise as shown in FIG. 4.

Figure 5:
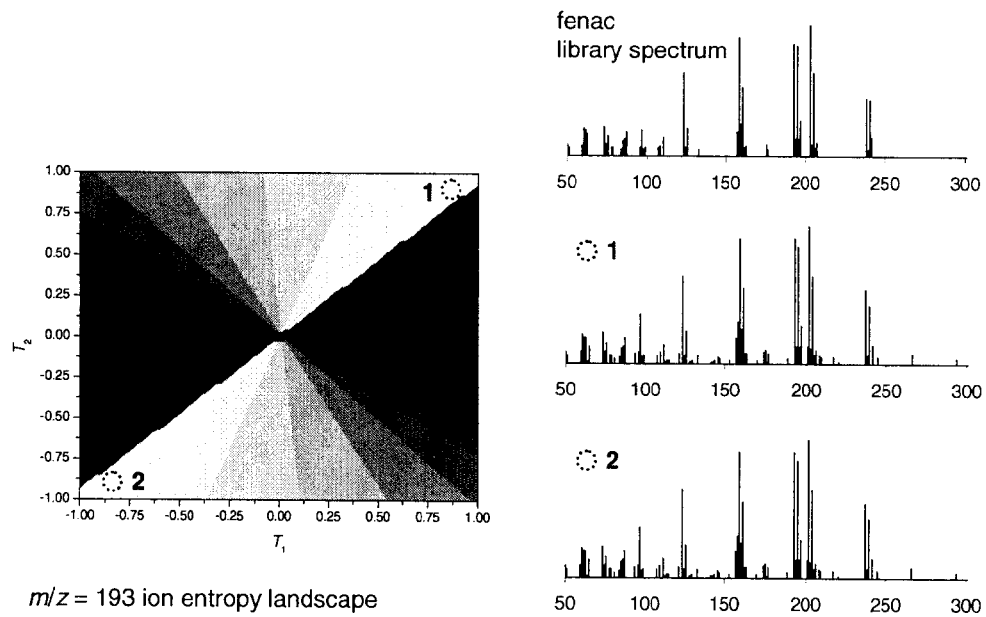
FIG. 5 depicts a visualization of the mass spectral entropy landscape in the space of the transformation vector T. 2D entropy plot of a two component system (pesticides fenac and sulfotep) where the two dimensions are the T coordinates and the third (shades of gray) is the entropy of the mass spectrum corresponding to these coordinates. Black area represents large entropy areas (and the forbidden area with negative entropy or negative component abundances) and white area represents low entropy (pure component regions). Ion m/z 193 is found in both component mass spectra (shared fragment ion).

The entropy landscape surface then was explored by calculating the entropy of arbitrary chosen fragment ion, say m/z=193. This ion is found in both component mass spectra so using this ion as target will extract the component with highest concentration, in this case fenac. The entropy surface plot for this ion is shown in FIG. 5. In FIG. 5, entropy of the extracted mass spectra using m/z=193 target ion is plotted as a function of the T vector (variables $T_1$ and $T_2$). White area corresponds to small entropy while black areas represent large entropy regions. It is evident that the entropy surface is smooth, regardless of the mass spectral noise. Also, there are formally two minima, however, due to the matrix multiplication properties, both yield identical extracted mass spectra. This is due to the fact that both minima correspond to vectors that differ only by the sign: in this example, $T \approx (-0.9, -0.9)$ and $T = (+0.9, +0.9)$. This means that for practical purposes it does not matter which minima if found since they both carry same physical meaning.

Example 3

Extraction of Simulated Four-Component Pesticide System

Unfortunately, visualizing the entropy landscape in more component systems is challenging as is any multidimensional visualization task. In this case, the four components are pesticides aldrin, bifenox, bromophos and captan. Chromatographic elution of the four pesticide mixture was simulated in silico. For this purpose, reference spectra of the pure compounds were obtained from the NIST database, and an overlapping chromatographic elution profile was then established with added noise. Concentration of the each component in this mixture was equal and severe chromatographic overlap was created. The obtained total ion current chromatogram is shown in FIG. 6.

Figure 6:
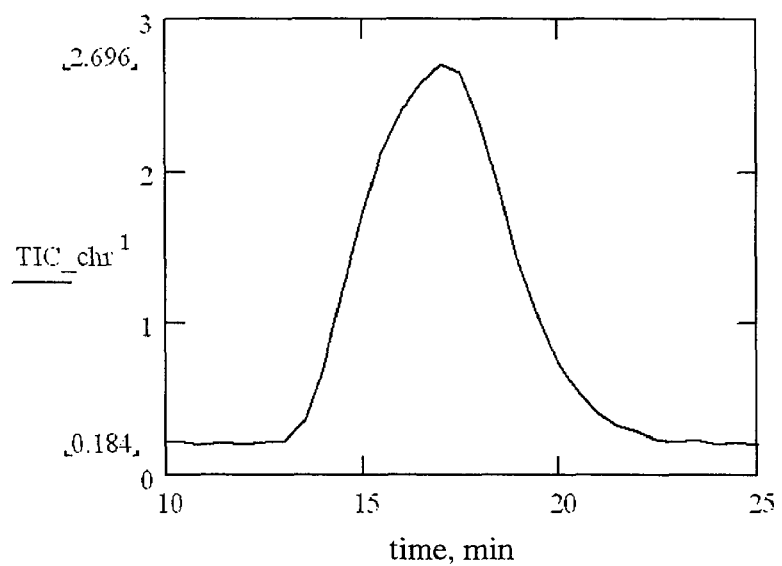
FIG. 6 depicts a simulated overlapping chromatographic elution profile for a mixture of aldrin, bromophos, bifenox and DDT.
Figure 7A:
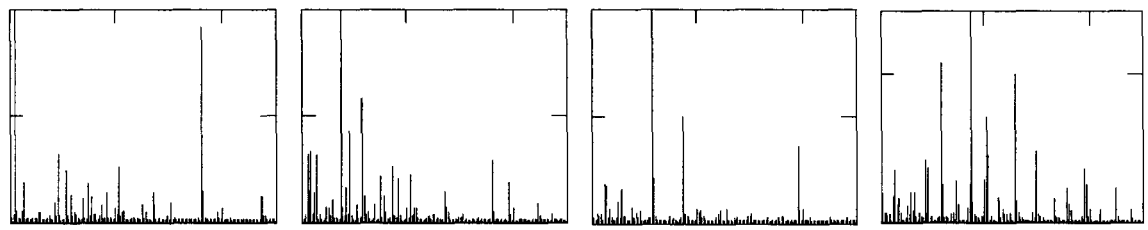
FIG. 7a depicts mass spectra for aldrin, bromophos, bifenox and DDT extracted from the simulated overlapping chromatographic elution profile of FIG. 6.
Figure 7B:
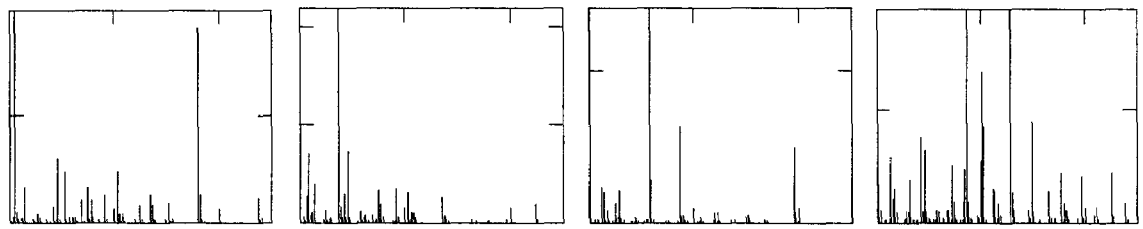
FIG. 7b depicts reference (library) mass spectra for aldrin, bromophos, bifenox and DDT.

From the chromatogram of FIG. 6, a mass spectrum was extracted for every given time interval (scan) and the band-target entropy minimization was performed without using any prior knowledge of the system. Four components were identified and their extracted spectra (FIG. 7a) agree well with the used library spectra (FIG. 7b).

Figures 8A, 8B:
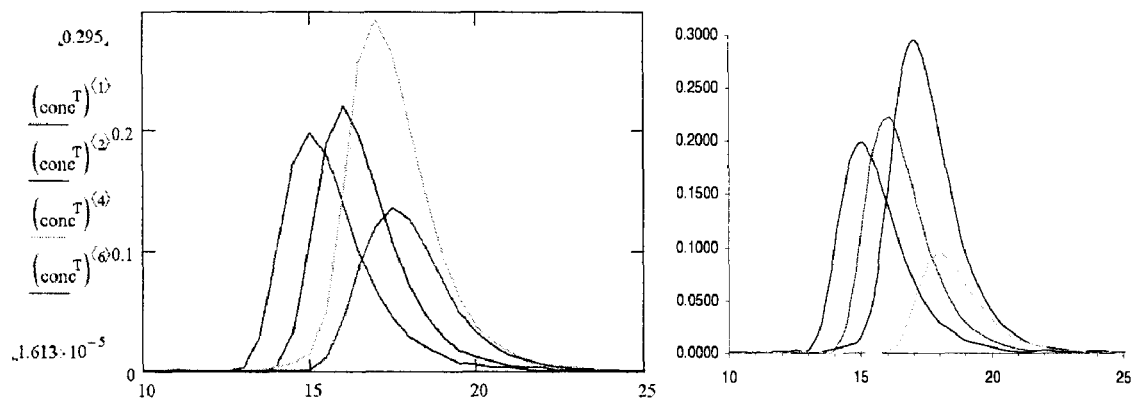
FIG. 8a depicts the deconvoluted single ion chromatograms of each component in the four component system of aldrin, bromophos, bifenox and DDT.
FIG. 8b depicts the values actually used for the simulation of the four component system of aldrin, bromophos, bifenox and DDT.

The deconvoluted single ion chromatograms of each component (FIG. 8a) also agree well with the values used for the simulation (FIG. 8b).

Figure 9A:
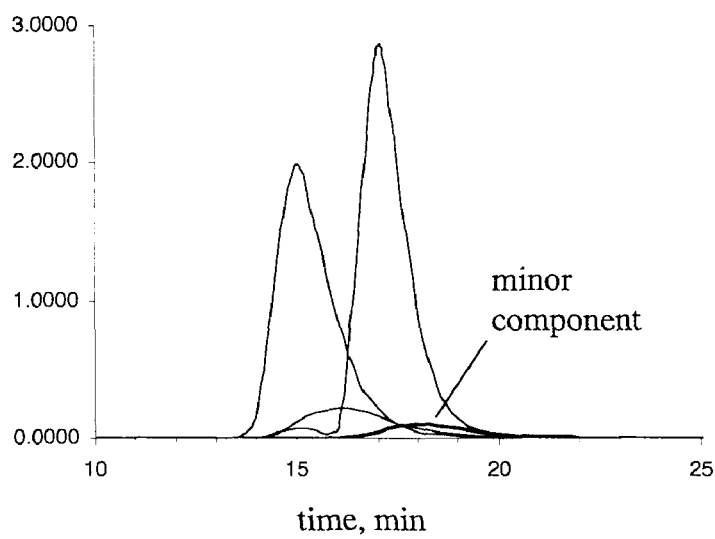
FIG. 9a a simulated chromatographic elution profile for a four-component mixture wherein one component is present at a level of 10%.
Figures 9B, 9C:
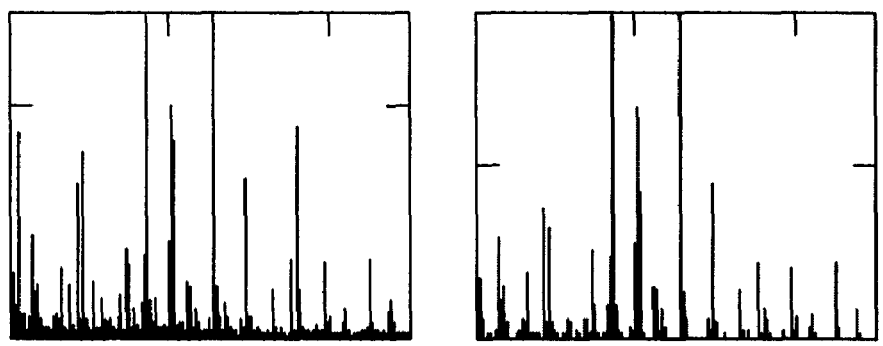

When a mixture of the same four components with added noise was simulated wherein one of the components is a minor component present at the 10% level, an elution profile as shown in FIG. 9a is obtained. Entropy minimization still yielded the mass spectra of all four pesticide components. The extracted mass spectrum of the minor component (FIG. 9b) agrees well with the experimental spectrum (FIG. 9c).

Example 4

Comparison of Stochastic Optimization to Directed Optimization in Blind Entropy Minimization For the system described in Example 3, the fact that the entropy landscape surfaces are monomodal can be proved also by the fact that many simplex minimizations each initialized randomly at different position leads to the same results, identical to the minimum entropy result obtained by exhaustive random search. Targeting the ion with the mass-to-charge ratio m/z=75 (major ion in bromophos mass spectrum), leads to the retrieval of bromophos mass spectrum each time. Global entropy minimum found by exhaustive random search in this case is close to that found using several directed optimization attempts; each initiated at random starting point. Same quality spectra were obtained using gradient-based directed optimization approaches, such as the steepest descent minimization. Results for the above four component system are summarized Table 2.

TABLE 2

Comparison of the spectral deconvolution time using various optimization approaches[a]

|  | Lowest entropy | CPU time | Lowest entropy | CPU time |
|---|---|---|---|---|
| Stochastic optimization | m/z = 185 |  | m/z = 75 |  |
| Exhaustive random search | 4.20 | 12.0 s | 8.94 | 11.6 s |
| Simulated annealing | 4.25 | 14.9 s | 8.91 | 15.8 s |
| Directed optimization |  |  |  |  |
| Downhill simplex | 4.24 | 0.16 s | 8.93 | 0.11 s |

[a]Four component pesticide mixture system. CPU time includes only the function optimization sub-routine.

Mass spectra obtained from directed and stochastic optimization approaches are identical with except to minor random noise. Hence, it is evident that directed downhill optimization strategies can be successfully used to find the pure component mass spectra without resort to general stochastic approaches, such as simulated annealing. One of the main difficulties in applying simulated annealing is that many choices have to be made concerning parameter values (tuning), which are not trivial and are quite often very poorly made by trial and error. Most crucially, one has to specify the temperature decrease profile (annealing schedule), and the initial temperature parameters. This can be rather sensitive to the minimization speed.

It has now been surprisingly found that the use of stochastic approaches such as simulated annealing is not necessary as direct optimization approaches can be successfully used. The gain in computing time of downhill simplex (a directed optimization approach) compared to simulated annealing from various tested systems is about 100 times (two orders of magnitude). The above outlined entropy surface properties (i.e. that the entropy landscape is monomodal (with no local minima)) leading to the usefulness of directed optimization approaches are not obvious a priori.

Example 5

Specific Compound Recognition

It is possible to use entropy minimization to recognize a specific compound from a complex mixture. Three components in a three component mixture have mass spectra as shown in FIGS. 10a-c. A component of interest (A) has an m/z 5 and m/z 7 ion ratio of 1:1 (FIG. 10a).

In this mixture, the component A itself is present in amounts of less than 1%, or, in other words, 99% of the signal is noise for spectral identification purposes. The ratio of ions m/z 5 and 7 in the present overlapping system varies from 0.54 to 0.38 during the elution of these three highly overlapping components. This means that visual detection of the component A is impossible from such system since the correct ion ratio (i.e. 1.00) is not observed in any of the individual mass spectrometry scans. Targeting the two ions m/z 5 and 7 for entropy minimization, however, can extract almost pure component spectrum as shown in FIG. 11.

In this example, the highest amount of the target compound in the chromatographic elution profile is about 1.5% whereas entropy minimization could purify this component up to 99%. The m/z 5 and 7 ion ratio in the extracted spectrum is from 0.95 to 1.03 depending on the actual simulated noise levels. FIG. 12a is the elution profile of the mixture and FIG. 12b is the mixture mass spectrum corresponding to the highest amounts of component A present (at 14.5 min elution time). Clearly, no pattern of component A can be recognized from this spectrum.

Such targeted retrieval of component helps to increase the analysis specificity. As a result, the number of false positive detections is decreased and number of positive detections is increased. The mere presence of correct two ion ratio within a mixture chromatogram does not guaranty the presence of the component with such ion ratios in its pure spectrum (false positive detection). This example shows that the presence of certain patterns can be detected by entropy minimization where the commonly used ion ratio approach fails.

Example 6

Rotation of Dimensions

Elution time and m/z scale can be swapped and entropy minimization performed in the time domain. In this way, pure peak elution profiles (usable for quantification of components) can be obtained rather than the mass spectra (usable for identification of components).

In this modification of the entropy minimization algorithm, the time domain is used as the variable space. In other words, the entropy minimization yields no longer pure component mass spectra but pure component chromatographic elution profiles. The modification is achieved by 90° rotation of the data matrix and the singular value decomposition is then performed on the rotated matrix. Band targeting is now performed for retention time (spectral scans).

Figure 13:
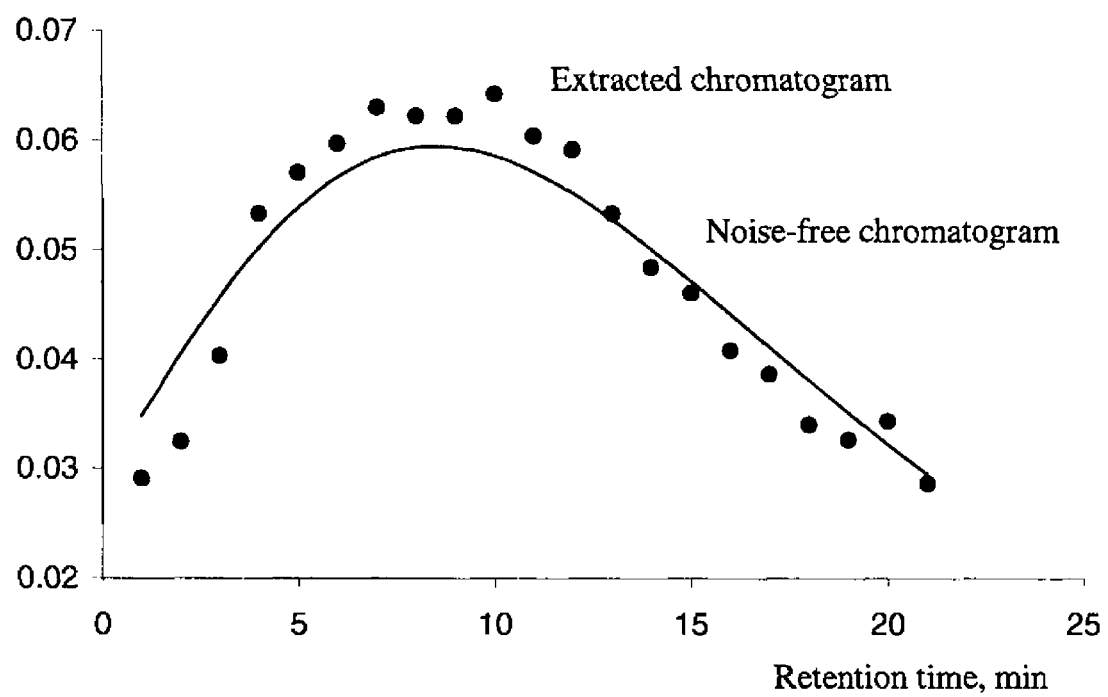
FIG. 13 depicts a noise-free chromatogram (line) representing a theoretical chromatographic profile used for simulation of a three-component mixture, and an extracted chromatogram (dots) from time domain entropy minimization.

Using the three-component system described in Example 5, the noise-free chromatogram (FIG. 13, line) represents the theoretical chromatographic profile used for simulation. To this, line noise was added and so were the other two overlapping components. The extracted chromatogram (FIG. 13, dots) is in good agreement with the actual pure component elution profiles. Hence, the concentration of components (peak area of the pure component chromatogram) can be estimated rather accurately.

REFERENCES

The following references are herein incorporated by reference.

Alfassi, Z. B. On the normalization of a mass spectrum for comparison of two spectra. *J. Am. Soc. Mass Spectrom.* 2004, 15, 385-387.

Brunengraber, H.; Kelleher, J. K.; Des Rosiers, C. Applications of mass isotopomer analysis to nutrition research. *Annu. Rev. Nutr.* 1997, 17, 559-596.

Chew, W.; Widjaja, E.; Garland, M. Band-Target Entropy Minimization (BTEM): An Advanced Method for Recovering Unknown Pure Component Spectra. Application to the FTIR Spectra of Unstable Organometallic Mixtures. *Organometallics* 2002, 21, 1982-1990.

Corana, A.; Marchesi, M.; Martini, C.; Ridella, S. Minimizing Multimodal Functions of Continuous Variables with the "Simulated Annealing" Algorithm. *ACM Trans. Math. Softw.* 1987, 13, 262-280.

D'Ulivo, A.; Mester, Z.; Sturgeon, R. E. The mechanism of formation of volatile hydrides by tetrahydroborate(III) derivatization: A mass spectrometric study performed with deuterium labeled reagents. *Spectrochim. Acta B.* 2005, 60, 423-438.

Duplan, J. C.; Mahi, L.; Brunet, J. L. NMR determination of the equilibrium constant for the liquid $H_2O-D_2O$ mixture. *Chem. Phys. Lett.* 2005, 413, 400-403.

Friedman, L.; Shiner, V. J. J. Experimental Determination of the Disproportionation of Hydrogen Isotopes in Water. *J. Chem. Phys.* 1966, 44, 4639-4640.

Guo, L.; Wiesmath, A.; Sprenger, P.; Garland, M. Development of 2D Band-Target Entropy Minimization and Application to the Deconvolution of Multicomponent 2D Nuclear Magnetic Resonance Spectra. *Anal. Chem.* 2005, 77, 1655-1662.

Harris, J. M.; Knorr, F. J. Multichannel detection and resolution of chromatographic peaks. U.S. Pat. No. 4,353,242 issued Oct. 12, 1982.

Iwata, T.; Koshoubu, J. Minimization of Noise in Spectral Data. *Appl. Spectrosc.* 1996, 50, 747-752.

Iwata, T.; Koshoubu, J. New Method to Eliminate the Background Noise from a Line Spectrum. *Appl. Spectrosc.* 1994, 48, 1453-1456.

Kirkpatrick, S.; Gelatt, D. D. J.; Vecchi, M. P. Optimization by simulated annealing. *Science* 1983, 220, 671-680.

Kushnir, M. M.; Rockwood, A. L., Nelson, G. J. Methods for quantitative analysis by tandem mass spectrometry. U.S. patent Publication published Jul. 28, 2005.

Lawson, C. L.; Hanson, R. J. Solving Least Squares Problems; Prentice Hall: Englewood Cliffs, N.J., 1974.

Lee, P. W.-N.; Byerley, L. O.; Bergner, A. E. Mass Isotopomer Analysis: Theoretical and Practical Considerations. *Biological Mass Spectrometry* 1991, 20, 451-458.

Libnau, F. O.; Christy, A. A.; Kvalheim, O. M. Determination of the Equilibrium Constant and Resolution of the HOD Spectrum by Alternating Least-Squares and Infrared Analysis. *Appl. Spectrosc.* 1995, 49, 1431-1437.

Meija, J.; Caruso, J. A. Deconvolution of Isobaric Interferences in Mass Spectra. *J. Am. Soc. Mass Spectrom.* 2004, 15, 654-658.

Meija, J.; Centineo, G.; Garcia Alonso, J. I.; Sanz-Medel, A.; Caruso, J. A. Interpretation of Butyltin Mass Spectra Using Isotope Pattern Reconstruction for The Accurate Measurement of Isotope Ratios From Molecular Clusters. *J. Mass Spectrom.* 2005, 40, 807-814.

Pappin, D. J. C.; Khainovski, N.; Spencer, D. D. Method and apparatus for de-convoluting a convoluted spectrum. U.S. Pat. No. 7,105,806 issued Sep. 12, 2006.

Schoen, A. E.; Cope, E. G.; Tinnon, J. E. Method and apparatus for the deconvolution of unresolved data. U.S. Pat. No. 5,247,175 issued Sep. 21, 1993.

Shannon, C. E.; Weaver, W. *The Mathematical Theory of Communication*; University of Illinois Press Chicago, 1949.

Sturgeon, R. E.; Mester, Z. Analytical Applications of Volatile Metal Derivatives. *Appl. Spectrosc.* 2002, 56, 202A-213A.

Widjaja, E.; Garland, M. Pure component spectral reconstruction from mixture data using SVD, global entropy minimization, and simulated annealing. Numerical investigations of admissible objective functions using a synthetic 7-species data set. *J. Comput. Chem.* 2002, 23, 911-919.

Widjaja, E.; Li, C.; Garland, M. Semi-Batch Homogeneous Catalytic In-Situ Spectroscopic Data. FTIR Spectral Reconstructions Using Band-Target Entropy Minimization (BTEM) without Spectral Preconditioning. *Organometallics* 2002, 21, 1991-1997.

Widjaja, E.; Li, C.; Chew, W.; Garland, M. Band-Target Entropy Minimization. A Robust Algorithm for Pure Component Spectral Recovery. Application to Complex Randomized Mixtures of Six Components. *Anal. Chem.* 2003, 75, 4499-4507.

Wolfsberg, M.; Massa, A. A.; Pyper, J. W. Effect of Vibrational Anharmonicity on the Isotopic Self-Exchange Equilibria $H_2X+D_2X=2HDX$. *J. Chem. Phys.* 1970, 53, 3138-3146.

Zhang, H.; Garland, M.; Zeng, Y.; Wu, P. Weighted two-band target entropy minimization for the reconstruction of pure component mass spectra: simulation studies and the application to real systems. *J. Am. Soc. Mass Spectrom.* 2003, 14, 1295-1305.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. A method of obtaining pure component mass spectra or pure peak elution profiles from mass spectra of a mixture of components comprising: estimating number of components in the mixture; filtering noise; and extracting individual component mass spectra or pure peak elution profiles using blind entropy minimization with direct optimization.

2. The method of claim 1, wherein the direct optimization comprises downhill simplex minimization.

3. The method of claim 1, wherein the number of components is estimated by singular value decomposition.

4. The method of claim 1, wherein the filtering of noise is accomplished by singular value decomposition.

5. The method of claim 1, further comprising quantifying amounts of the components in the mixture.

6. The method of claim 1, further comprising comparing a reference mass spectrum to the extracted individual component mass spectra to identify a specific component of the mixture.

7. The method of claim 6, wherein the specific component comprises an illicit substance, an explosive, a drug or an environmental pollutant.

8. The method of claim 1, wherein the entropy minimization is performed in m/z domain to obtain the pure component mass spectra.

9. The method of claim 1, wherein the entropy minimization is performed in elution time domain to obtain the pure peak elution profiles.

10. The method of claim 1, wherein the mass spectra of the mixture of components comprises mass spectra of the mixture at various component concentrations obtained by partial physical separation of the components.

11. The method of claim 10, wherein the partial physical separation is achieved using gas chromatography, liquid chromatography, electrophoresis, ion mobility, distillation, gas effusion, crystallization or a combination thereof.

12. The method of claim 1, wherein the mass spectra of the mixture of components are obtained using atmospheric ionization mass spectrometry or vacuum ionization mass spectrometry.

13. The method of claim 1, wherein the mass spectra of the mixture of components are obtained using electrospray ionization mass spectrometry, atmospheric pressure chemical ionization mass spectrometry, MALDI mass spectrometry, electron impact ionization mass spectrometry or chemical ionization mass spectrometry.

14. The method of claim 1, wherein the mass spectra of the mixture of components are obtained using electrospray ionization high energy fragmentation mass spectrometry.

15. The method of claim 1, wherein the mass spectra of the mixture of components are GC/MS spectra of overlapping or partially overlapping compounds.

16. The method of claim 1, wherein the mass spectra of the mixture of components are GC/MS spectra of overlapping or partially overlapping isotopologues.

17. The method of claim 1, wherein the mass spectra of the mixture of components are mass spectra of overlapping or partially overlapping proteins or metabolites.

18. The method of claim 1, wherein the mass spectra in the set are mass spectra of overlapping or partially overlapping peptides.

19. The method of claim 1, wherein the mass spectra of the mixture of components are mass spectra of overlapping or partially overlapping pesticides.

20. The method of claim 1, wherein the mass spectra of the mixture of components are MALDI mass spectra from a single solution having multiple components.

21. A computer readable medium containing instructions for carrying out the method as defined in claim 1.

* * * * *